United States Patent
Biber

(10) Patent No.: US 9,448,295 B2
(45) Date of Patent: Sep. 20, 2016

(54) MULTI-LAYER CUSHION FOR OPTIMUM ADJUSTMENT TO ANATOMY AND FOR SUSCEPTIBILITY ADJUSTMENT

(71) Applicant: Stephan Biber, Erlangen (DE)

(72) Inventor: Stephan Biber, Erlangen (DE)

(73) Assignee: Siemens Aktiengesellschaft, München (DE)

(*) Notice: Subject to any disclaimer, the term of this patent is extended or adjusted under 35 U.S.C. 154(b) by 493 days.

(21) Appl. No.: 13/847,763

(22) Filed: Mar. 20, 2013

(65) Prior Publication Data

US 2013/0249559 A1    Sep. 26, 2013

(30) Foreign Application Priority Data

Mar. 21, 2012  (DE) .................. 10 2012 204 527

(51) Int. Cl.
| | | |
|---|---|---|
| *G01V 3/00* | (2006.01) | |
| *G01R 33/387* | (2006.01) | |
| *G01R 33/34* | (2006.01) | |
| *A61B 5/055* | (2006.01) | |
| *G01R 33/565* | (2006.01) | |
| *G01R 33/56* | (2006.01) | |

(52) U.S. Cl.
CPC .......... *G01R 33/387* (2013.01); *A61B 5/055* (2013.01); *A61B 5/0555* (2013.01); *G01R 33/34084* (2013.01); *G01R 33/56536* (2013.01); *G01R 33/5607* (2013.01)

(58) Field of Classification Search
CPC ............................................... G01R 33/34084
USPC .................................................. 324/318, 322
See application file for complete search history.

(56) References Cited

U.S. PATENT DOCUMENTS

| | | | | |
|---|---|---|---|---|
| 5,396,905 | A * | 3/1995 | Newman et al. | 600/422 |
| 6,943,551 | B2 | 9/2005 | Eberler et al. | |
| 7,002,347 | B2 * | 2/2006 | Feiweier et al. | 324/318 |
| 7,132,829 | B2 * | 11/2006 | Hudson et al. | 324/318 |
| 2005/0228210 | A1 | 10/2005 | Muntermann | |
| 2008/0214930 | A1 | 9/2008 | Brasile | |
| 2011/0006769 | A1 | 1/2011 | Iwasa et al. | |
| 2012/0323113 | A1 | 12/2012 | Biber | |
| 2013/0193968 | A1 | 8/2013 | Biber | |

FOREIGN PATENT DOCUMENTS

| | | |
|---|---|---|
| CN | 1512902A A | 7/2004 |
| CN | 101957438A A | 1/2011 |
| DE | 10314215 B4 | 11/2006 |
| WO | WO 2008114195 A2 | 9/2008 |

OTHER PUBLICATIONS

German Office Action dated Nov. 16, 2012 for corresponding German Patent Application No. DE 10 2012 204 527.9 with English translation.
Garc C. Lee et al., "Pyrolytic Graphite Foam: A Passive Magnetic Susceptibility Matching Material," Journal of Magetic Resonance Imaging, vol. 32, pp. 684-691, (2010).

(Continued)

*Primary Examiner* — Louis Arana
(74) *Attorney, Agent, or Firm* — Lempia Summerfield Katz LLC

(57) ABSTRACT

A shim cushion for a magnetic resonance tomography system includes at least two layers. A first layer of the at least two layers includes both a higher deformability and also a lower susceptibility than a second layer of the at least two layers.

29 Claims, 3 Drawing Sheets

(56) References Cited

OTHER PUBLICATIONS

C. Juchem et al., "Dynamic Multi-Coil Shimming of the Human Brain at 7 Tesla", Proc. Intl. Soc. Mag. Reson. Med. 19 (2011).
S-K. Lee et al.,"B0 Shimming in 3 T Bilateral Breast Imaging with Local Shim Coils", Proc. Intl. Soc. Mag. Reson. Med. 19 (2011).
Gary Lee et al., "Improved Frequency Selective Fat Suppression in the Cervical Spine and Neck with Tissue Susceptibility Matched Pyrolytic Graphite Foam," Musculoskeletal ISMRM 20th Annual Meeting, May 8, 2012.
Chinese office Action for related Chinese Application No. 201310091016.3 dated Feb. 1, 2016, with English Translation.
Korean Notice of Allowance for related Korean Application No. 10 2013 0029791 dated Mar. 9, 2016, with English Translation.
Korean Office action for related Korean Application No. 10-2013-0029791, dated Oct. 27, 2015, with English Translation.

* cited by examiner

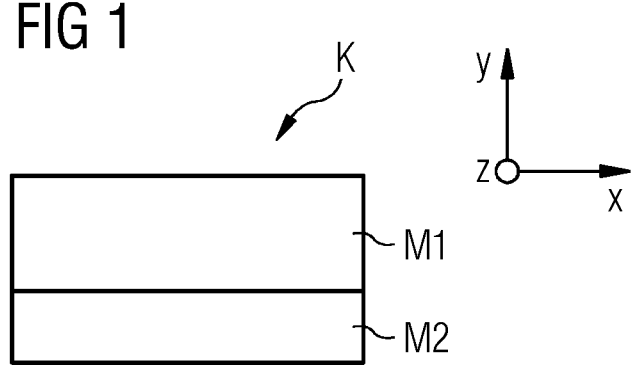
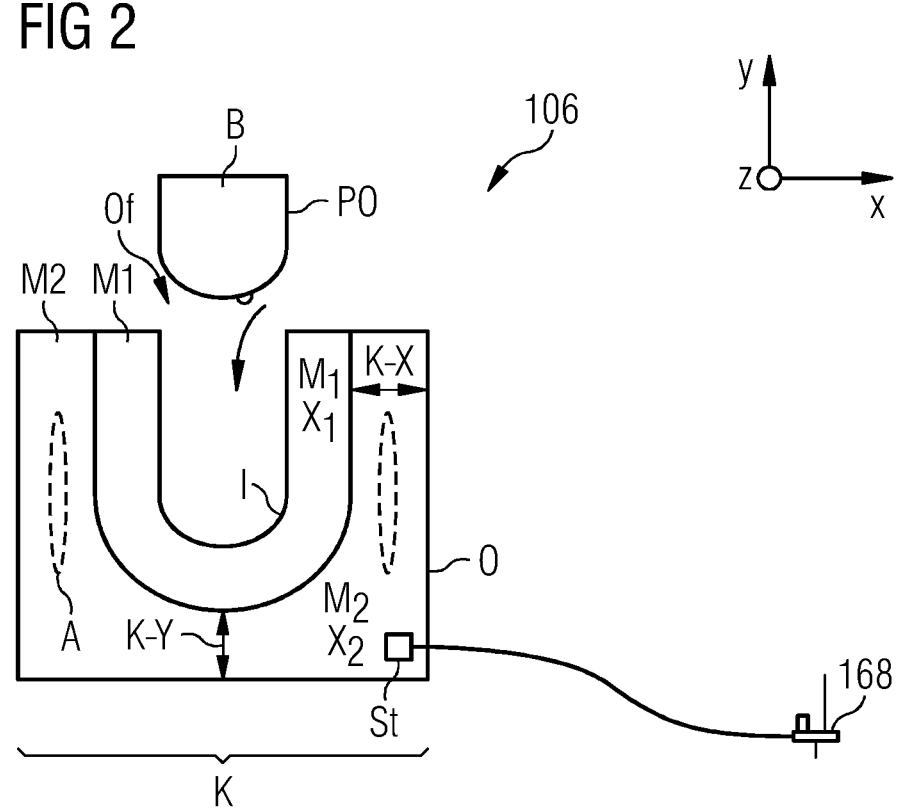

FIG 3A
FIG 3B
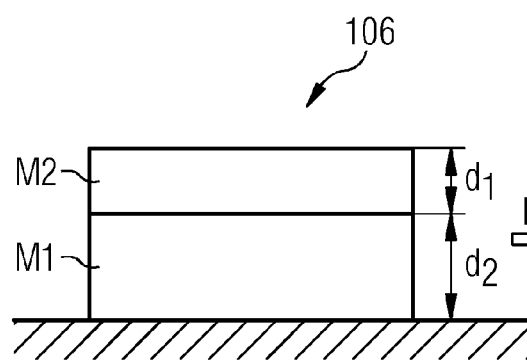
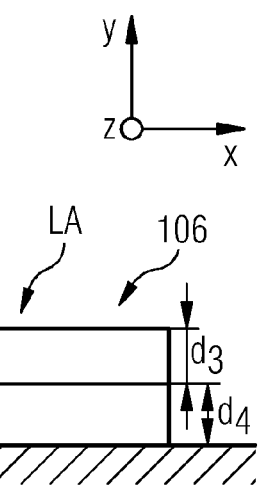
$$\frac{d_4}{d_2} < \frac{d_3}{d_1}$$

MULTI-LAYER CUSHION FOR OPTIMUM ADJUSTMENT TO ANATOMY AND FOR SUSCEPTIBILITY ADJUSTMENT

This application claims the benefit of DE 10 2012 204 527.9, filed on Mar. 21, 2012, which is hereby incorporated by reference.

BACKGROUND

The present embodiments relate to a magnetic resonance tomography (MRT) shim cushion.

Magnetic resonance devices (MRTs) for examining objects or patients using magnetic resonance tomography are known, for example, from DE10314215B4.

SUMMARY

The present embodiments may obviate one or more of the drawbacks or limitations in the related art. For example, magnetic resonance tomography (MRT) imaging is optimized.

BRIEF DESCRIPTION OF THE DRAWINGS

FIG. 1 shows one embodiment of a flat cushion made of a foam material having two layers that include different mechanical properties and magnetic susceptibilities;

FIG. 2 shows one embodiment of a local coil with a cushion having an opening for a chest of a patient;

FIG. 3 shows, to the left (FIG. 3a), two exemplary layers of a cushion detensioned without load and, to the right (FIG. 3b), the two layers of a cushion deformed under load.

DETAILED DESCRIPTION

Figure 4:
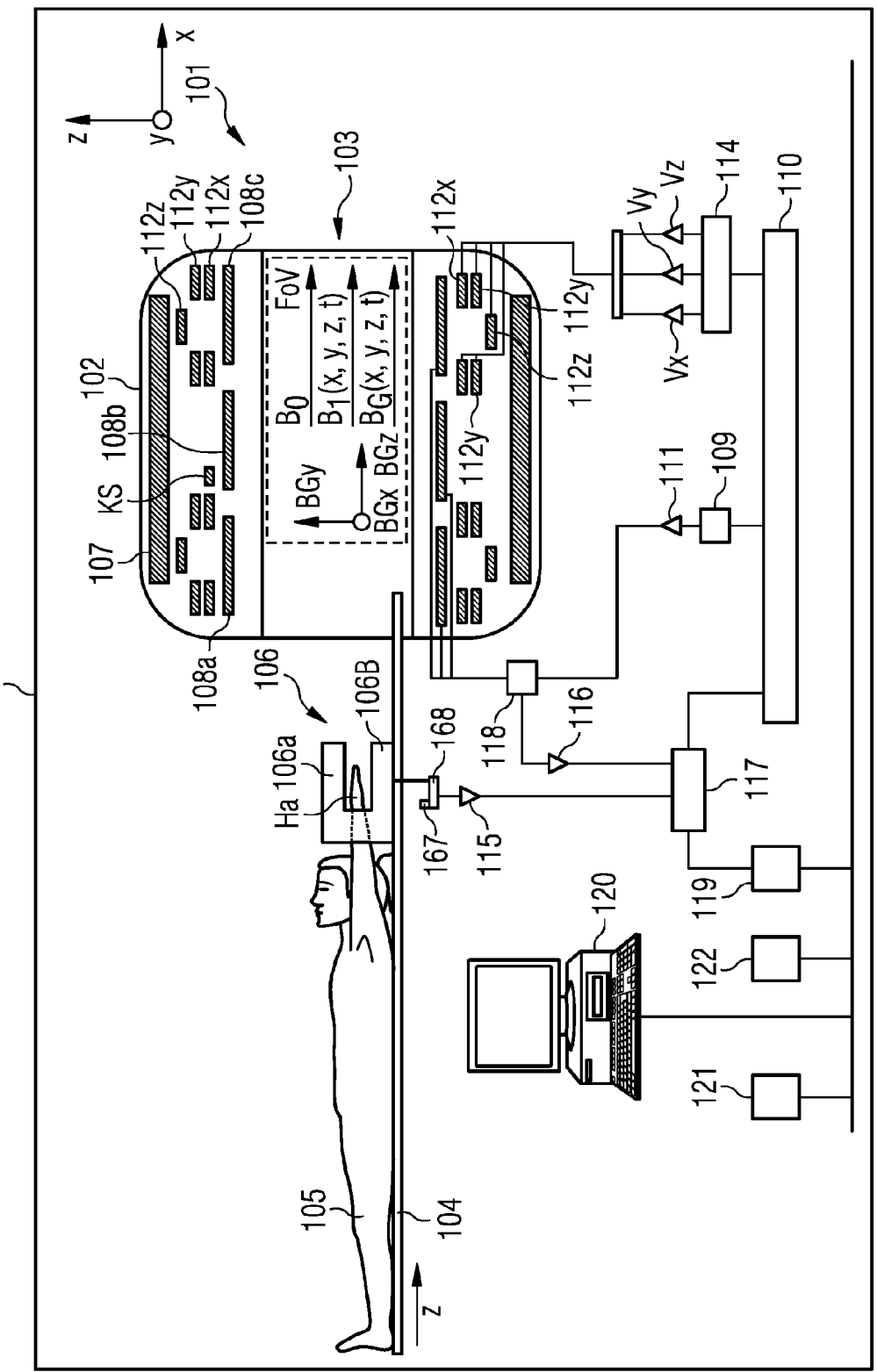
FIG. 4 shows a schematic representation of an MRT system.

FIG. 4 shows an imaging magnetic resonance device MRT 101 (e.g., located in a shielded room or Faraday cage F) having a whole body coil 102 with a tubular space 103, for example, into which a patient couch 104 with a body 105 (e.g., of an examination object such as a patient (a hand Ha of the patient)) may be moved in the direction of arrow z (e.g., with or without local coil arrangement 106 such as two-piece hand coil 106A, 106B) in order to generate recordings of the patient 105 using an imaging method. A local coil arrangement 106 is arranged, for example, on the patient. Recordings of a sub area of the body 105 may be generated in a field of view (FOV) in a local area of the MRT with the local coil arrangement 106. Signals of the local coil arrangement 106 may be evaluated (e.g., converted into images, stored or displayed) by an evaluation device (e.g., including elements 168, 115, 117, 119, 120, 121) of the MRT 101, which may be connected to the local coil arrangement 106 via coaxial cables or radio, for example.

In order to examine a body 105 (e.g., an examination object or a patient) using a magnetic resonance device MRT 101 with magnetic resonance imaging, different magnetic fields that are attuned as precisely as possible to one another in terms of temporal and spatial characteristics are irradiated onto the body 105. A strong magnet (e.g., a cryomagnet 107) in a measuring cabin with a tunnel-shaped opening 103, for example, generates a strong static main magnetic field $B_0$ that amounts, for example, to 0.2 Tesla to 3 Tesla or even more. A body 105 to be examined is mounted on a patient couch 104 in an approximately homogeneous area of the main magnetic field B0 in the field of view. Excitation of the nuclear spin of atomic nuclei of the body 105 takes place via high frequency magnetic excitation pulses B1(x, y, z, t) that are irradiated via a high frequency antenna (and/or if necessary, a local coil arrangement) shown simplified as body coil 108 (e.g., multi-piece body coil 108a, 108b, 108c). High frequency excitation pulses are generated, for example, by a pulse generation unit 109 that is controlled by a pulse sequence control unit 110. Following amplification by a high frequency amplifier 111, the high frequency pulses are routed to the high frequency antenna 108. The high frequency system shown in FIG. 4 is only shown schematically. In other embodiments, more than one pulse generation unit 109, more than one high frequency amplifier 111 and several high frequency antennae 108a, b, c are used in a magnetic resonance device 101.

The magnetic resonance device 101 has gradient coils 112x, 112y, 112z, with which during a measurement, magnetic gradient fields $B_G$(x, y, z, t) are irradiated for selective slice excitation and for local encoding of the measuring signal. The gradient coils 112x, 112y, 112z are controlled by a gradient coil control unit 114 that, similarly to the pulse generation unit 109, is connected to the pulse sequence control unit 110.

Signals emitted by the excited nuclear spin (e.g., of the atomic nuclei in the examination object) are received by the body coil 108 and/or at least one local coil arrangement 106, amplified by assigned high frequency amplifier 116 and further processed and digitalized by a receive unit 117. The recorded measured data is digitalized and stored as complex numerical values in a k-space matrix. An associated MR image may be reconstructed from the k-space matrix populated with values using a multidimensional Fourier transformation.

For a coil that may be operated both in the transmit and/or also in the receive mode (e.g., the body coil 108 or a local coil 106), the correct signal forwarding is controlled by an upstream transmit-receive switch 118.

An image processing unit 119 generates an image from measured data, which is shown to a user via a control console 120 and/or is stored in a storage unit 121. A central computing unit 122 controls the individual system components.

Images with a high signal-to-noise ratio (SNR) may be recorded in MR tomography using local coil arrangements (e.g., coils, local coils). These are antenna systems that are attached in the immediate vicinity on (anterior) or below (posterior) or on or in the body 105. During an MR measurement, the excited nuclei induce a voltage into the individual antennae of the local coil. The induced voltage is amplified with a low-noise preamplifier (e.g., LNA, Preamp) and forwarded to the receive electronics. Hgh field systems (e.g., 1.5T-12T or more) are also used in highly-resolved images to improve the signal-to-noise ratio. If more individual antennae may be connected to an MR receive system than there are receivers present, a switching matrix (e.g., RCCS receive channel coil selector) is integrated between the receive antennae and receiver (e.g., a switching matrix). This routes the currently active receive channels (e.g., the receive channels that lie precisely in the field of view of the magnet) to the existing receiver. As a result, more coil elements than there are receivers present may be connected, since with a whole body coverage, only the coils that are located in the field of view and/or in the homogeneity volume of the magnetic are to be read out.

An antenna system that may include, for example, an antenna element or as an array coil including a number of antenna elements (e.g., coil elements) may be referred to as a local coil arrangement 106. These individual antenna elements are embodied, for example, as loop antennae (loops), butterfly, flexible coils or saddle coils. A local coil arrangement includes, for example, coil elements, a pre-amplifier, further electronics (e.g., decoupling coil), a housing, contacts and may include a cable with a plug, by which the local coil arrangement is connected to the MRT system. A receiver 168 attached on the system side filters and digitalizes a signal received by a local coil 106 (e.g., by radio) and transfers the data to a digital signal processing device that may derive an image or a spectrum from the data obtained from a measurement and makes the image or spectrum available to the user for subsequent diagnosis by the user and/or storage, for example.

Imaging in magnetic resonance tomography (MRI) relates to spins of atomic nuclei aligned in a $B_0$ base field. For many applications, the homogeneity of the base field (e.g., same field intensity in a large three-dimensional space) is of decisive importance for the image quality and also for the spatial registration of images (e.g., distortions).

The use of fat saturation techniques is decisive of the diagnostic validity of many imaging techniques. For example, the fatty tissue, which issues a strong signal in many types of contrast, is faded out. The "fading out" of fatty tissue by fat saturation techniques may indicate the diagnostic evaluatability of the MR images, since pathological tissue in many sequence types indicates similar or identical contrast behavior to fat.

An efficiently-functioning fat saturation is of importance for many questions.

There are various known methods of fat saturation such as, for example, Dixon or spectral fat saturation. With spectral fat saturation and techniques used, the fact that fat and water have slightly different resonance frequencies (e.g., deviation of the resonance frequency: fat from water approximately 3.1 ppm) is used. A strong transmit pulse on the fat frequency may suppress the signal of the fat without influencing the imaging of the protons pertaining to the water molecules. The functionality of all techniques, which relate to the spectral separation of fat and water, nevertheless depends on the homogeneity of the base field. If the base field varies in a similar degree of magnitude to the spectral separation of fat and water (e.g., 3.1 ppm), the fat and water resonances (e.g., within an image/field of view) lie on the same frequency and may no longer be spectrally separated.

Super-conducting magnets allow for magnetic field homogeneities with deviations of less than 1 ppm across a volume of approximately 30×40×50 cm. Problems with fat saturation may therefore exist in far outer lying areas of anatomy (e.g., shoulder), which may also not be mounted centrally on account of the lack of space in the bore of an MR magnet.

The inhomogeneities introduced by the tissue of the patient may nevertheless be more critical than the known and deterministic $B_0$ inhomogeneities of the base field. Human tissue exhibits relative magnetic permeability that differs by 1.0000000. As a result, the discontinuities of air and tissue may, for example, result in strong $B_0$ distortions. The inhomogeneous distribution of water/air/bones/fat in the human body may also result in a distortion of the $B_0$ field that differs for each patient.

A number of approaches exist as a solution to this problem Shim coils may be used on the system or local shim coils may be used in the vicinity of the patient. Passive materials, the susceptibility of which is adjusted to the human tissue, may also be used. Foam materials may be advantageous here, since foam materials have a low weight and may be produced at low cost and with definable magnetic properties. Graphite-filled cushions made of foam materials may be used. A compression of these graphite-filled cushions nevertheless results in a change in the susceptibility of the graphite-filled cushions.

Two advantages, for example, may be achieved by one or more of the present embodiments.

A high degree of deformability of the cushion may be achieved, so that the cushion is optimally pressed against the body even with various sizes of anatomy.

A low variation in the susceptibility may simultaneously be achieved despite high deformability.

A deformation (e.g., a compression) of a graphite-filled cushion may result in a higher graphite-volume density and may therefore result in an unwanted change in the susceptibility.

Dixon techniques may be used for fat-water separation.

In one embodiment, a multi-layer cushion structure of a cushion K, in which a part of the cushion that is to be used for susceptibility matching (e.g., susceptibility adjustment by graphite filling of filling with other diamagnetic materials such as bismuth, carbon nanotubes, graphs) is close to the patient and may be less easily compressed than a layer disposed therebelow (e.g., further from the patient), may be provided. As a result, a good adjustment to the susceptibility may be achieved in the immediate vicinity of the region of the patient to be examined, and the compression (e.g., with a relatively large anatomy of the patient) is simultaneously recorded by the layer disposed therebelow. Multi-layer cushions, in which each layer has its own mechanical properties (e.g., compressibility, solidity) and magnetic properties (e.g., different susceptibility) may be provided. A continuous transition of mechanical properties and/or magnetic properties that is already directly processed in the plastic may also be provided.

A use of a multi-layer cushion K with a low graphite concentration close to the coil and susceptibility-matched (e.g., with respect to the susceptibility-adjusted) properties (e.g., more graphite) to the body surface may also be advantageous in terms of reducing ohmic losses that are caused by the graphite in the coil, since the cushion areas near to the coil couple lower losses to the coil (e.g., lower conductivity).

Instead of graphite, another diamagnetic, or depending on the desired field distortion, also paramagnetic or ferromagnetic, material may also be used.

One advantage of an embodiment may be in the mechanical and magnetic structure of a cushion that allows for an optimal molding to the patient using compression and increases the $B_0$ homogeneity by the magnetic properties and at the same time allows for a large compressibility with low deviations in the susceptibility of the cushion.

FIG. 1-3 show embodiments of shim cushions. FIG. 1 shows a flat shim cushion made of a foam material having two layers M1 and M2 that have different mechanical properties and magnetic susceptibilities. The shim cushion K may be arranged, for example, between an area of a patient to be examined and a local coil (e.g., on one or both sides of a hand and outside of the cushion on one or both sides of part of a hand local coil) or may be an integral part (e.g., patient surface close to and/or inside) of a local coil.

FIG. 2 shows a simplified schematic representation of a local coil 106 with a two-layer MRT shim cushion K (e.g., fastened therein or removable therefrom) having an opening Of, into which a chest B of a patient 105 may be inserted, where the chest B is surrounded on at least two sides by the local coil and/or the Shim cushion.

FIG. 2 shows an integral part of the local coil 106 (e.g., a cushion K with two layers M1 and M2) that have different mechanical properties and magnetic susceptibilities (X1, X2). Antenna A and/or a controller St of the local coil 106 may be contained, for example, in one of at least two layers of the cushion K (e.g., outside) or a further outer lying layer of the cushion or of the local coil (e.g., in which the cushion may be arranged internally).

FIG. 3 shows to the left (FIG. 3a) two layers M1, M2 of a cushion K detensioned without a load acting thereupon. To the right (FIG. 3b), FIG. 3 shows these two layers of a cushion K deformed under load LA (e.g., a deforming force by pressing on or contacting the local coil with the patient or contacting the patient 105, Ha on the local coil).

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A shim cushion for a magnetic resonance tomography system, the shim cushion comprising:
at least two layers, wherein a first layer of the at least two layers has a higher deformability and a lower susceptibility than a second layer of the at least two layers.

2. The shim cushion as claimed in claim 1, wherein the second layer, which is further remote from a patient surface in a system on the patient than the first layer, has both a higher deformability and also a lower susceptibility than the first layer, which is closer to the patient surface with the system provided on the patient.

3. The shim cushion as claimed in claim 1, wherein the higher deformability of the first layer contains a higher elastic compressibility, a higher elastic deformability, or a higher compressibility and deformability than the second layer.

4. The shim cushion as claimed in claim 1, wherein a ratio of a diameter of the first layer in an uncompressed state to a diameter of the first layer in a state compressed by a load is greater than a ratio of a diameter of the second layer in an uncompressed state relative to a diameter of the second layer in a state compressed by a load.

5. The shim cushion as claimed in claim 1, wherein the shim cushion has an arched cross-section.

6. The shim cushion as claimed in claim 5, wherein the arched cross-section is U-shaped.

7. The shim cushion as claimed in claim 6, wherein the U-shaped cross-section has an opening for receiving a body part on one side.

8. The shim cushion as claimed in claim 1, further comprising a third layer disposed on an interior of the shim cushion, the third layer having a lower deformability and a higher susceptibility than the further layer, the second layer being disposed on an exterior of the shim cushion.

9. The shim cushion as claimed in claim 1, wherein the first layer is further remote from a patient surface in a system provided on the patient than the second layer, and
wherein the first layer and the second layer each have a diameter of at least 0.1 cm.

10. The shim cushion as claimed in claim 9, wherein the first layer and the second layer each have a diameter of at least 0.2 cm.

11. The shim cushion as claimed in claim 10, wherein the first layer and the second layer each have a diameter of at least 0.3 cm.

12. The shim cushion as claimed in claim 11, wherein the first layer and the second layer each have a diameter of at least 0.5 cm.

13. The shim cushion as claimed in claim 12, wherein the first layer and the second layer each have a diameter of at least 1 cm.

14. The shim cushion as claimed in claim 13, wherein the first layer and the second layer each have a diameter of at least 2 cm.

15. The shim cushion as claimed in claim 1, wherein one or more layers of the at least two layers of the shim cushion contains a diamagnetic material.

16. The shim cushion as claimed in claim 15, wherein the diamagnetic material comprises a diamagnetic material composed of or including graphite.

17. The shim cushion as claimed in claim 1, wherein the first layer comprises more diamagnetic material than the second layer.

18. The shim cushion as claimed in claim 17, wherein the diamagnetic material comprises graphite.

19. The shim cushion as claimed in claim 1, wherein the second layer is further remote from a patient surface in a system provided on the patient than the first layer, and
wherein the second layer has less diamagnetic material than the first layer.

20. The shim cushion as claimed in claim 1, wherein only the first layer, only the second layer, or both the first layer and the second layer contain a foam material.

21. The shim cushion as claimed in claim 20, wherein the foam material includes graphite powder that is distributed in the foam material.

22. The shim cushion as claimed in claim 1, wherein only the first layer, only the second layer, or both the first layer and the second layer include plastic.

23. The shim cushion as claimed in claim 1, wherein only the first layer, only the second layer, or both the first layer and the second layer include plastic with a continual transition in the plastic of mechanical properties, magnetic properties, or mechanical properties and magnetic properties.

24. The shim cushion as claimed in claim 1, wherein the at least two layers comprise at least three layers.

25. The shim cushion as claimed in claim 1, wherein the shim cushion is operable to be elastically compressed in one direction, in two directions orthogonal to one another, or in three directions orthogonal to one another.

26. The shim cushion as claimed in claim 1, wherein the shim cushion forms an integral part of a magnetic resonance tomography local coil.

27. The shim cushion as claimed in claim 26, wherein the integral part is an integral part of a hand coil, a wrist coil, a chest coil, a shoulder coil, a neck coil, an ankle coil, or a head coil.

28. The shim cushion as claimed in claim 1, wherein the shim cushion is a magnetic resonance tomography shim cushion.

29. A magnetic resonance tomography local coil comprising:
a shim cushion comprising:
at least two layers, wherein a first layer of the at least two layers has a higher deformability and a lower susceptibility than a second layer of the at least two layers.

* * * * *